US009798368B2

(12) United States Patent
Barthe et al.

(10) Patent No.: US 9,798,368 B2
(45) Date of Patent: *Oct. 24, 2017

(54) METHOD AND SYSTEM FOR ENHANCING COMPUTER PERIPHERAL SAFETY

(71) Applicant: Ardent Sound, Inc., Mesa, AZ (US)

(72) Inventors: Peter G. Barthe, Phoenix, AZ (US); Michael H. Slayton, Tempe, AZ (US); Vadim Kouklev, Tempe, AZ (US); Paul M. Jaeger, Mesa, AZ (US)

(73) Assignee: ARDENT SOUND, INC., Mesa, AZ (US)

( * ) Notice: Subject to any disclaimer, the term of this patent is extended or adjusted under 35 U.S.C. 154(b) by 303 days.

This patent is subject to a terminal disclaimer.

(21) Appl. No.: 14/519,886

(22) Filed: Oct. 21, 2014

(65) Prior Publication Data

US 2015/0198990 A1    Jul. 16, 2015

Related U.S. Application Data

(63) Continuation of application No. 13/453,847, filed on Apr. 23, 2012, now Pat. No. 8,868,958, which is a (Continued)

(51) Int. Cl.
*G06F 1/26* (2006.01)
(52) U.S. Cl.
CPC .............. *G06F 1/263* (2013.01); *G06F 1/266* (2013.01); *A61B 2560/0214* (2013.01)
(58) Field of Classification Search
CPC ............ A61B 5/00; G06F 1/263; G06F 1/266
See application file for complete search history.

(56) References Cited

U.S. PATENT DOCUMENTS 5,995,348 A * 11/1999 McCartan .............. H02H 9/025
361/115

* cited by examiner

*Primary Examiner* — Albert Wang
(74) *Attorney, Agent, or Firm* — Quarles & Brady LLP

(57) ABSTRACT

A method and system for enhancing computer peripheral safety is provided. In accordance with various aspects of the present invention, the exemplary method and system are configured to monitor and/or isolate alternating current (A.C.) supplies with and/or from any peripheral subsystems or devices. An exemplary method and system comprises an A.C. supply, a host computer system, and a peripheral subsystem or device connected to the host computer system, such as an ultrasound imaging and/or therapy peripheral, and an isolation subsystem configured for monitoring and/or isolating the A.C. supply from the peripheral subsystem or device. In accordance with an exemplary embodiment, an isolation subsystem comprises application software and associated modules and functions that when executed continuously monitors and/or polls the host computer's hardware and/or operating system for the presence of an isolated source, such as a battery, or an unisolated power source, such as through a battery charger and/or other connection path to the A.C. main supply. In accordance with other exemplary embodiments, an isolation subsystem can comprises a wireless or other safe/isolated electrical link for connecting a patient contact device, and/or a verification link or other verification mechanisms configured between an isolation transformer and host computer to monitor or observe usage to power the host computer and peripheral subsystem.

15 Claims, 12 Drawing Sheets

Related U.S. Application Data continuation of application No. 12/509,254, filed on Jul. 24, 2009, now Pat. No. 8,166,332, which is a continuation of application No. 11/380,161, filed on Apr. 25, 2006, now Pat. No. 7,571,336.

(60) Provisional application No. 60/674,964, filed on Apr. 25, 2005.

METHOD AND SYSTEM FOR ENHANCING COMPUTER PERIPHERAL SAFETY

CROSS-REFERENCE TO RELATED APPLICATIONS

This application claims priority to and is a continuation U.S. patent application Ser. No. 13/453,847, filed Apr. 23, 2012, entitled "Method and System for Enhancing Computer Peripheral Safety," and issued on Oct. 21, 2014 as U.S. Pat. No. 8,868,958, which claims priority to and is a continuation of U.S. patent application Ser. No. 12/509,254, filed Jul. 24, 2009, entitled "Treatment System for Enhancing Safety of Computer Peripheral for Use with Medical Devices by Isolating Host AC Power," and issued on Apr. 24, 2012 as U.S. Pat. No. 8,166,332, which claims priority to and is a continuation of U.S. patent application Ser. No. 11/380,161, filed Apr. 25, 2006, entitled "Method and System for Enhancing Safety with Medical Peripheral Device by Monitoring of Host Computer is AC Powered," and issued Aug. 4, 2009, as U.S. Pat. No. 7,571,336, which claims priority to and the benefit of U.S. Provisional Application No. 60/674,964, filed on Apr. 25, 2005, entitled "Method and System for Enhancing Computer Peripheral Safety," all of which are incorporated by reference herein.

FIELD OF INVENTION

The present invention relates to computer peripherals and in particular to a method and system for enhancing electrical safety of peripheral systems and devices, such as those used for medical applications.

BACKGROUND OF THE INVENTION

Personal computers, or PCs, have become ubiquitous and exist in forms such as desktop, notebook (laptop), or several ultra-portable configurations among others. This pervasiveness has led to the development of a large assortment of increasingly sophisticated peripherals. In general, computer peripherals are devices that connect to a computing system to facilitate certain tasks and/or implement features not contained within the standard or base computer, including medical devices and other like equipment. However, the stringent electrical safety requirements and regulations which exist for medical equipment has circumscribed their use with PCs as peripherals. For example, electrical leakage currents must be severely limited to maintain patient isolation, yet computers and their peripherals are not commonly designed to accommodate such restrictions. One approach to alleviate these requirements is to employ an isolation transformer to power the computer and peripherals, but such a solution is expensive, bulky in size and weight, and relatively unsuited to portability. An alternative of custom-made power supplies is impractical, since a manufacturer of peripherals cannot design isolated power supplies for all conceivable PCs. What is needed is an effective means of providing computer peripheral safety.

SUMMARY OF THE INVENTION

A method and system for enhancing computer peripheral safety is provided. In accordance with various aspects of the present invention, the exemplary method and system are configured to monitor and/or isolate alternating current (A.C.) supplies with and/or from any peripheral subsystems or devices. An exemplary method and system comprises an A.C. supply, a host computer system, and a peripheral subsystem or device connected to the host computer system, such as an ultrasound imaging and/or therapy peripheral, and an isolation subsystem configured for monitoring and/or isolating the A.C. main supply from the peripheral subsystem or device.

In accordance with an exemplary embodiment, an isolation subsystem comprises application software and associated modules and functions that when executed continuously monitors and/or polls the host computer's hardware and/or operating system for the supply of power from an isolated power source, such as a battery supply, or from an unisolated power source, such as connection through a battery charger and/or other connection path to the A.C. main supply. If a connection to the A.C. main supply is detected, the application software shuts down or otherwise isolates the peripheral subsystem, thereby disallowing usage on a patient, and/or provides suitable warnings to a system user, such as requiring confirmation that an isolation subsystem/hardware is connected or operating. In accordance with an exemplary embodiment, the application software can also comprise A.C. detection modules configured to monitor the state of A.C. or battery power, to monitor the battery level, and give appropriate warnings and guidance to the user to facilitate control of any peripheral hardware or devices.

In accordance with another exemplary embodiment, an isolation subsystem comprises a wireless or other safe/isolated electrical link for connecting a patient contact device, such as a medical probe, to the peripheral subsystem to assure a high degree of isolation between the patient and electronics.

In accordance with another exemplary embodiment, an isolation subsystem comprises a verification link or other verification mechanisms configured between an isolation transformer and host computer to monitor or observe usage to power the host computer and peripheral subsystem.

BRIEF DESCRIPTION OF THE DRAWINGS

The subject matter of the invention is particularly pointed out in the concluding portion of the specification. The invention, however, both as to organization and method of operation, may best be understood by reference to the following description taken in conjunction with the accompanying drawing figures, in which like parts may be referred to by like numerals.

DETAILED DESCRIPTION

The present invention may be described herein in terms of various functional components and processing steps. It should be appreciated that such components and steps may be realized by any number of hardware components and software features configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of computer peripheral contexts and that the exemplary embodiments relating to a method for enhancing computer peripheral safety as described herein for medical probes and applications are merely indicative of exemplary applications for the invention. For example, the principles, features and methods discussed may be applied to any computer application and peripheral.

Figure 1:
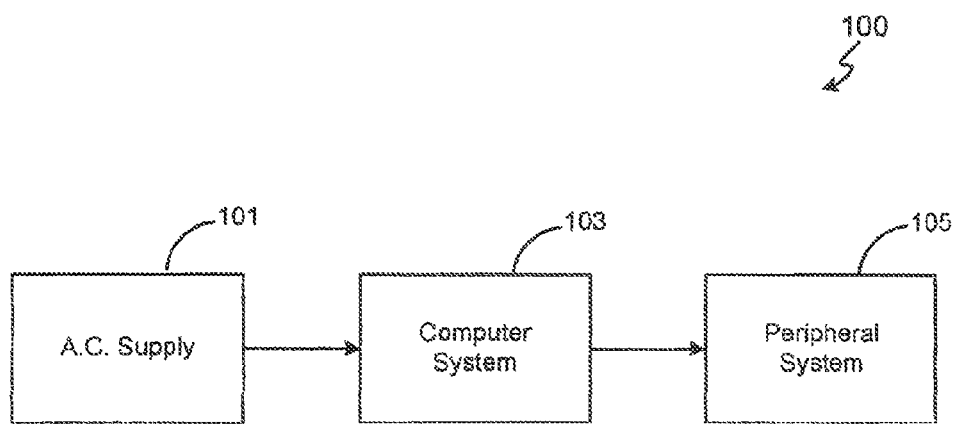
FIG. 1 is a block diagram of an exemplary system for enhancing electrical safety of peripheral systems in accordance with an exemplary embodiment of the present invention.

In accordance with various aspects of the present invention, a method and system for enhancing computer peripheral safety is provided. For example, in accordance with an exemplary embodiment, with reference to FIG. 1, an exemplary system 100 comprises an A.C. supply 101, a host computer system 103, and a peripheral subsystem or device 105 connected to host computer system 103. A.C. supply 101 suitably comprises an A.C. main supply or any other A.C. power source for supplying electrical power to equipment. Host computer system 103 is coupled to A.C. supply 101 and can comprise portable, laptop and/or notebook computers, desktop computers or any other host or operating computer configuration for operating peripheral subsystems and/or devices. Peripheral subsystem 105 can comprise any peripheral system or device, such as an ultrasound imaging and/or therapy peripheral system or device. For example, peripheral subsystem 105 can comprise systems and devices such as described in U.S. Pat. No. 6,440,071, entitled "Peripheral Ultrasound Imaging System", and hereby incorporated by reference. A host-peripheral communication link 106 can be operatively coupled between host computer 103 and peripheral subsystem 105 to facilitate control of peripheral subsystem 105, and can comprise any communication link or mechanism used between computers and peripheral devices for supplying power and/or communications. For example, communication link 106 can comprise a medical application link, such as for operatively coupling medical imaging and/or imaging/therapy systems to computer systems. To facilitate computer peripheral safety, system 100 further comprises an isolation subsystem configured for monitoring and/or isolating the A.C. supply 101 from peripheral subsystem 105.

Figure 2A:
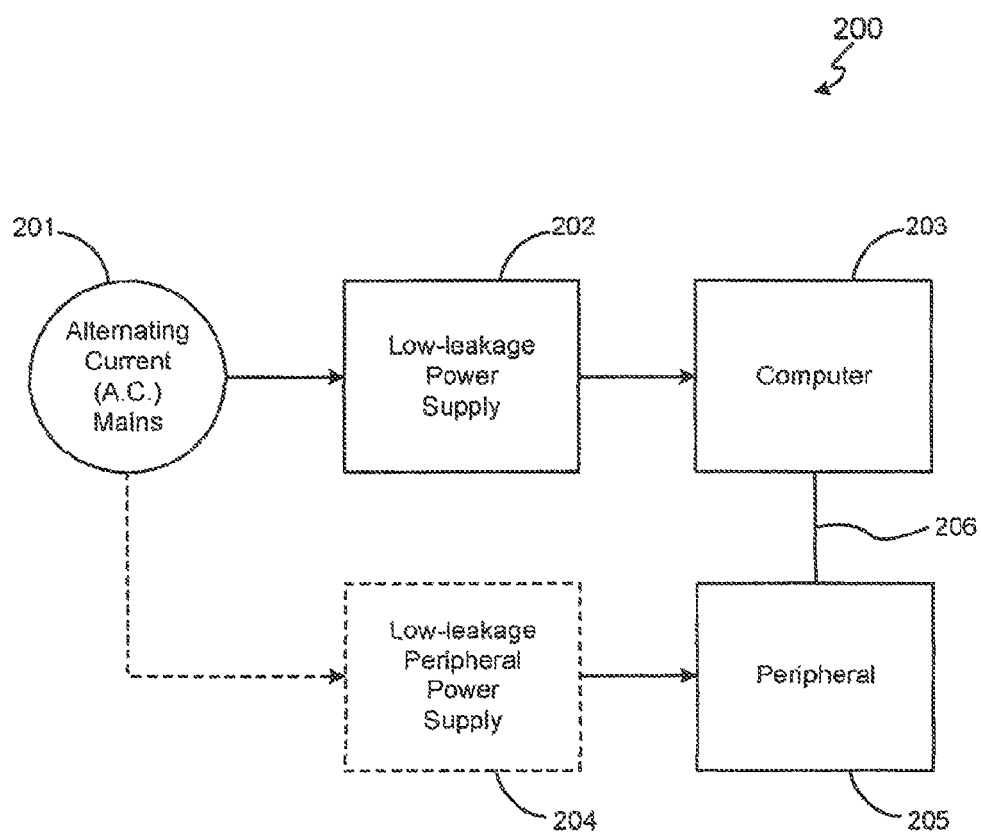
FIGS. 2A and 2B are block diagrams of a host computer, peripheral subsystem, power supplies and alternating current (A.C.) main supply for use with an isolation subsystem in accordance with an exemplary embodiment of the present invention.
Figure 2B:
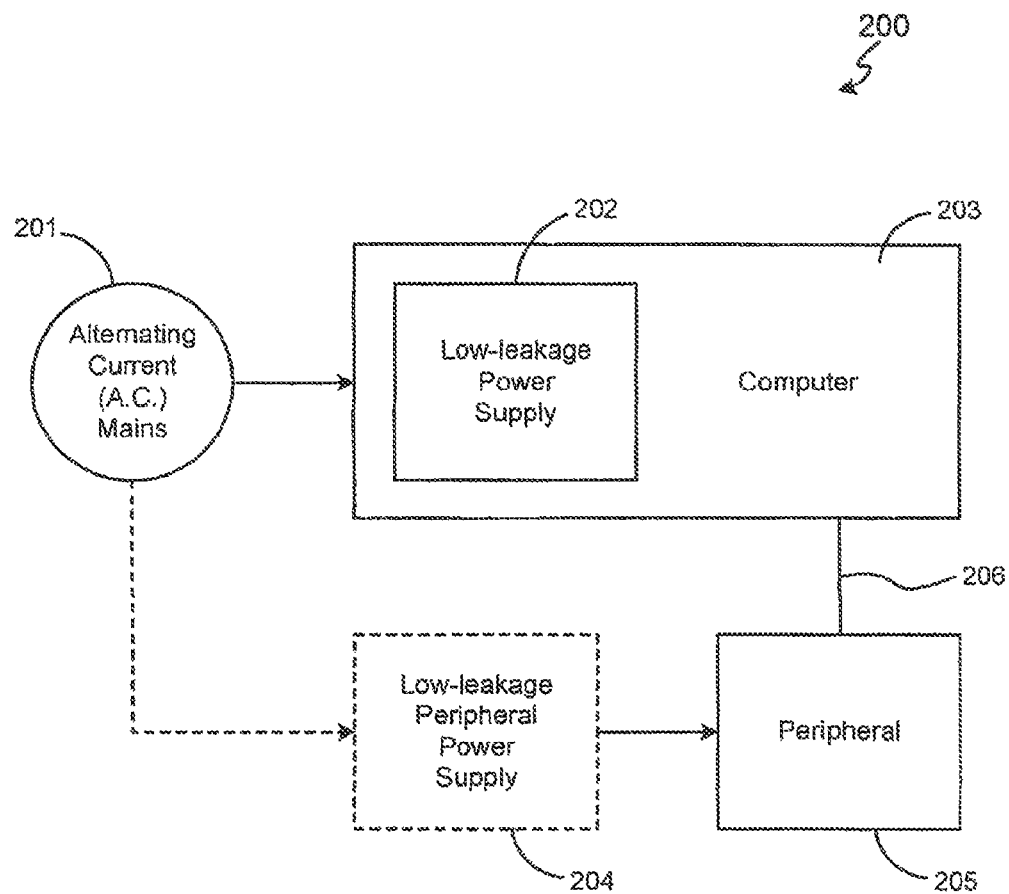

System 100 and components, A.C. supply 101, host computer 103 and peripheral 105, can be configured in various manners with an isolation subsystem for enhancing the safety of peripheral 105. For example, in accordance with an exemplary embodiment of the present invention, with reference to FIG. 2A, a peripheral safety system 200 can comprise a laptop or notebook computer 203 powered via a low-leakage/medical-grade power supply 202 that may also include a battery-backup system, including battery charger, or other uninterruptible power supply mechanism for host computer 203. Low-leakage/medical-grade power supply 202 can be suitably powered from A.C. main supply 201. In addition, an optional low-leakage/medical-grade peripheral power supply 204, powered from A.C. main supply 201, can also be coupled to peripheral 205 when additional power is needed for peripheral 205 and cannot be provided via communication link 206. Low leakage/medical-grade power supply 202 refers to a power supply or source of power which satisfies electric safety standards such as low-leakage, grounding, dielectric isolation, resistance to high potential voltages and transients. With reference to FIG. 2B, instead of laptop or notebook computers, host computer 203 can suitably comprise a desktop-style host computer and associated software 203. Typically desktop-style systems 203 differ from notebook-style systems in that power supply 202 is normally contained within the enclosure of computer 203.

An isolation subsystem can also be configured in various manners for monitoring and/or isolating A.C. supply 201 from peripheral subsystem or device 205. For example, to facilitate computer peripheral safety, a high degree of electrical isolation in one or both power supplies 202 and 204 can be provided, thus enhancing patient safety.

Figure 3:
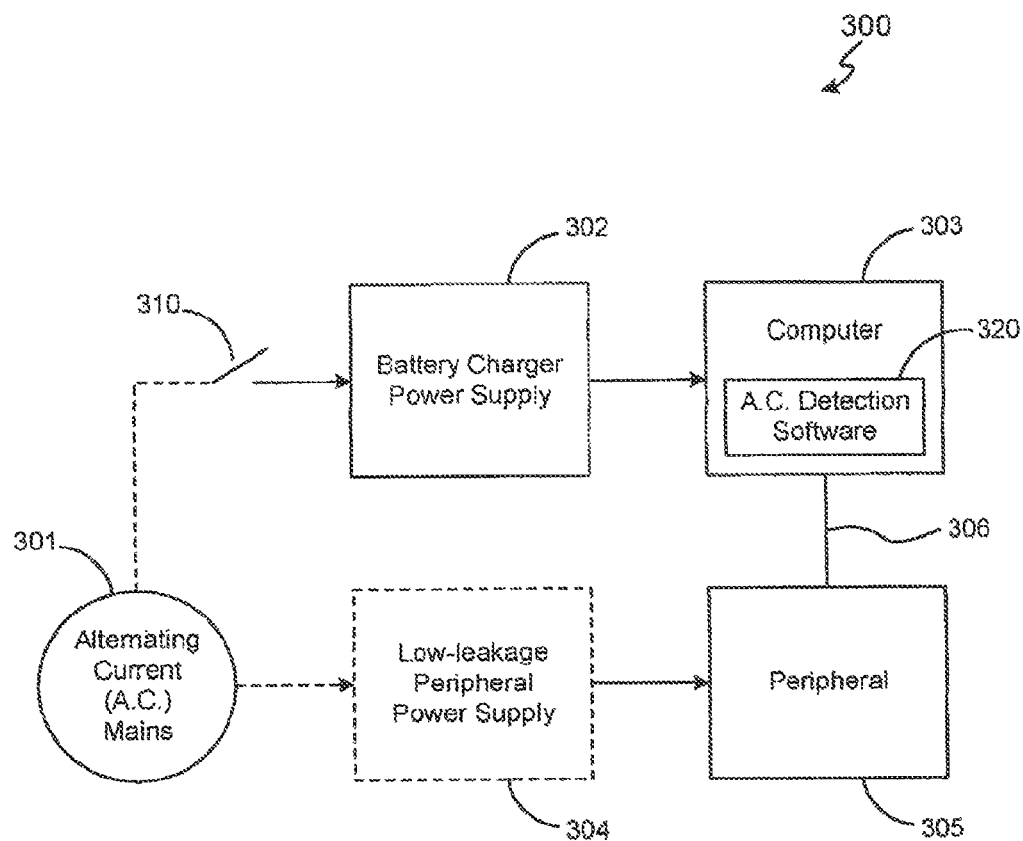
FIG. 3 is a block diagram of an exemplary system for enhancing electrical safety of peripheral systems with an isolation subsystem comprising A.C. detection software module in accordance with an exemplary embodiment of the present invention.

In accordance with another exemplary embodiment, with reference to FIG. 3, a peripheral safety system 300 can comprise a computer host and associated software 303 with an isolation subsystem comprising an A.C. detection software component 320. In this exemplary embodiment, host computer 303 is suitably powered via computer power supply/battery charger 302, powered from A.C. main 301. Power supply/battery charger 302 is configured to charge batteries for supplying an isolated power source to host computer 303. A.C. detection software component 320 is configured to detect through input devices 310 when PC battery charger 302 is connected to the A.C. main supply 301 (an unisolated power source) or disconnected (wherein an isolated power source comprising the charged battery supplies power) to the A.C. main supply 301 and disables (or re-enables) peripheral 305, e.g., disable or re-enable a medical application's functions. A.C. detection software component 320 can comprise any software and/or hardware configuration, including various input/output signals and components, for detecting when an A.C. supply is providing the source of power to host computer 303, e.g., detecting when a battery charger is connected and/or disconnected to A.C. main 301, and for suitably disabling one or more peripheral application functions, or otherwise for providing suitable warnings or other recommendations to the system user. By disabling at least some software/peripheral functionality, a high degree of electrical isolation is realized, and thus the patient safety is enhanced in medical applications.

Figure 4A:
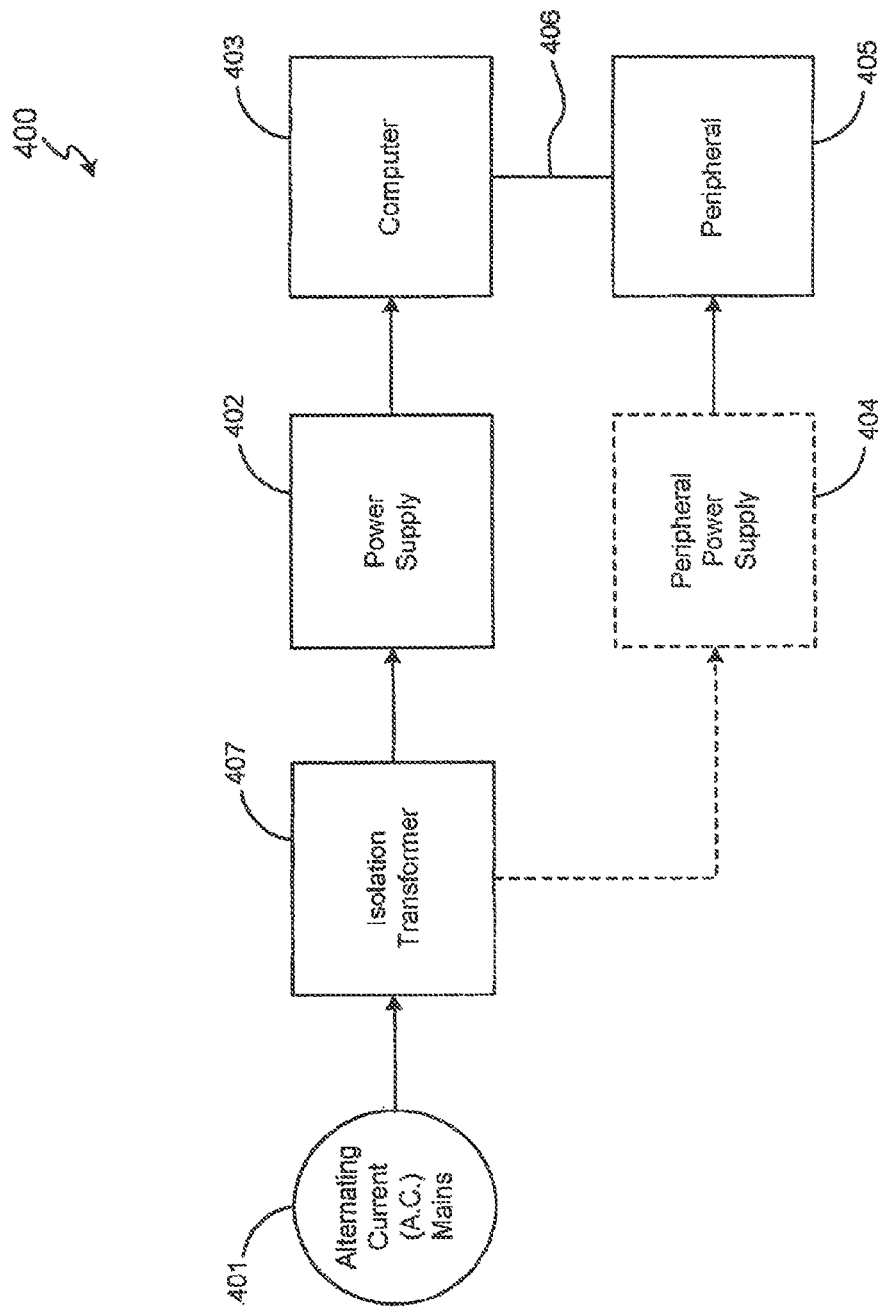
FIGS. 4A and 4B are block diagrams of exemplary systems for enhancing electrical safety of peripheral systems with an isolation subsystem and an isolation transformer in accordance with an exemplary embodiment of the present invention.
Figure 4B:
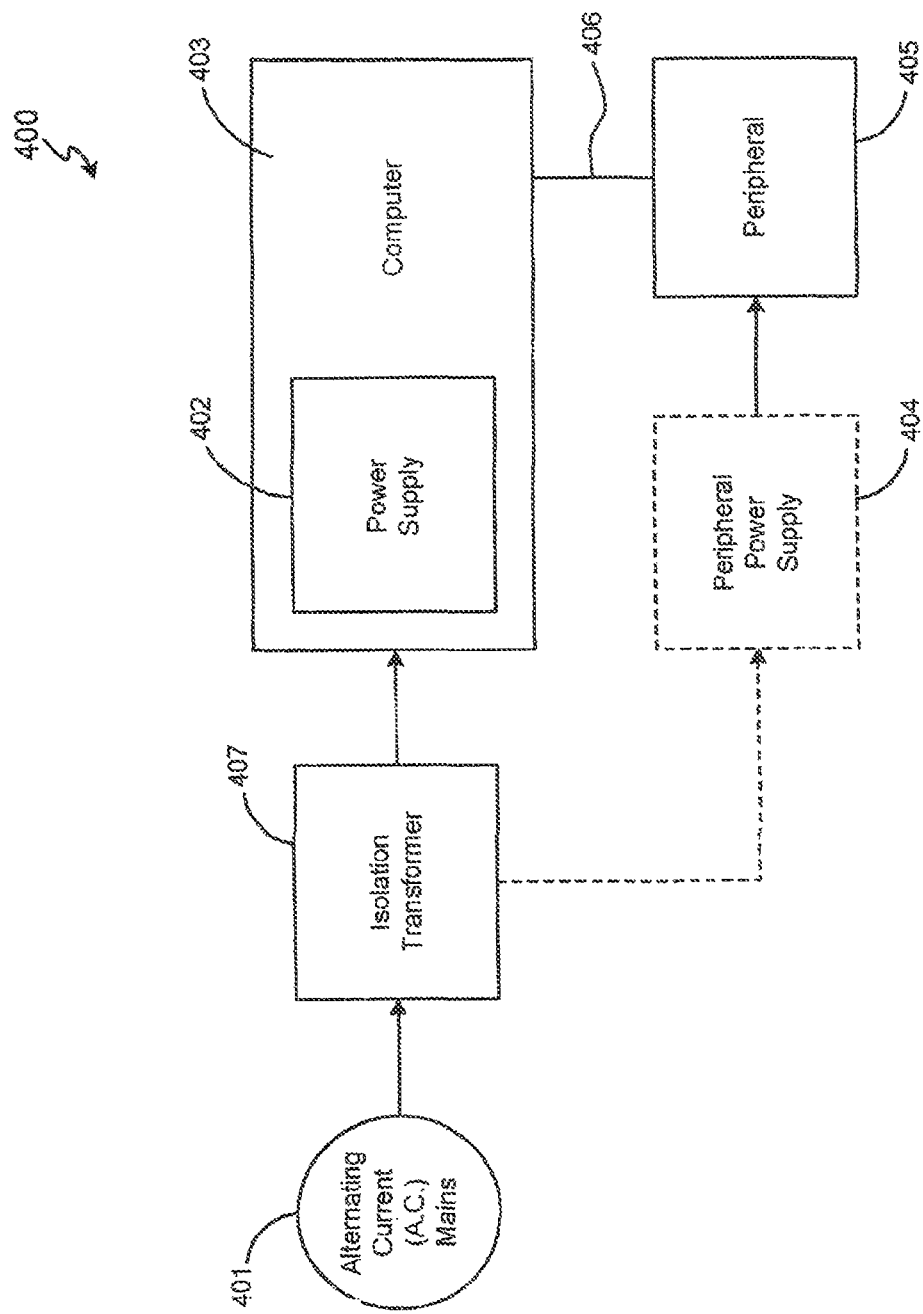

A.C. detection module 320 can be configured in addition to other isolation equipment and devices for facilitating safety. For example, with reference to FIGS. 4A and 4B, A.C. detection software can be resident within a laptop or notebook computer (FIG. 4A) or a desktop computer (FIG. 4B), with computer 403 further coupled to or including a power supply 402 coupled to an isolation transformer 407. Isolation transformer 407 can comprise any transformer configuration for isolating A.C. supplies from electrical equipment, such as computers and peripherals.

Figure 5A:
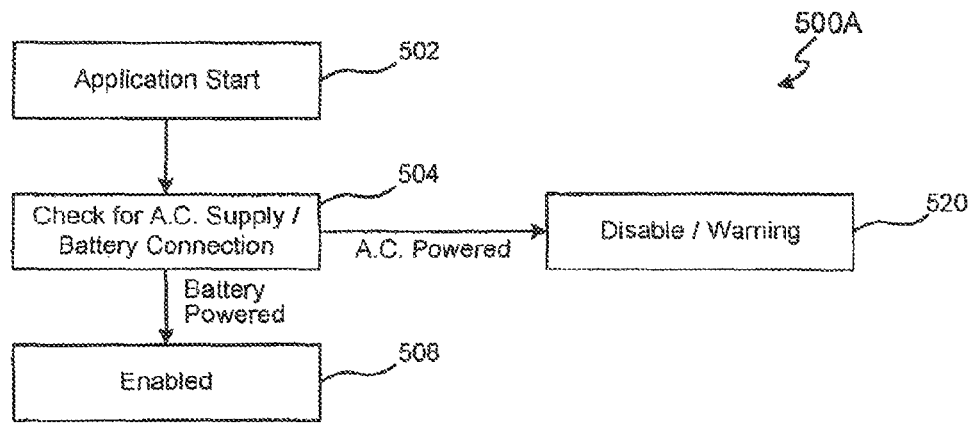
FIGS. 5A and 5B are flowcharts of operation for exemplary A.C. detection software modules in accordance with an exemplary embodiment of the present invention.

Detection module 320 can be provided in various operational steps through use of one or more algorithms and/or input/output devices for providing a method for enhancing computer peripheral safety. For example, with reference to FIG. 5A, in accordance with an exemplary embodiment, an exemplary method 500A may comprise A.C. detection module configured into application software and associated modules. As soon as the application software initiates or starts 502, the detection module checks for operative connection to an unisolated power source, e.g., an A.C. supply, or to an isolated power source, e.g., battery power 504. If not battery powered (i.e., if powered by or otherwise operatively connected to the A.C. supply, such as through the battery charger) the detection module moves to disabling functions and/or displaying a warning 520. However, if detection module determines the host computer is powered directly by battery power (e.g., the batter charger is not plugged in to the A.C. supply) 506, all normal hardware and software functionality is enabled 508, and the system continues operating.

Figure 5B:
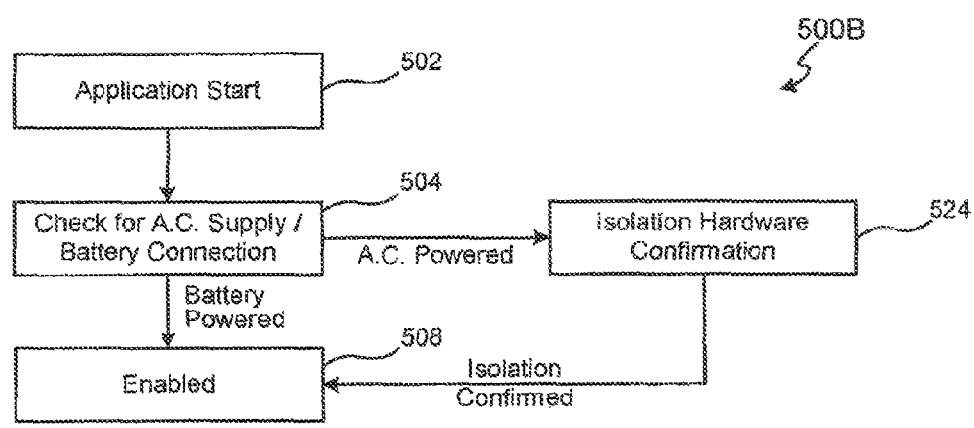

In accordance with another exemplary embodiment, with reference to FIG. 5B, instead of disabling functions or warning the system user to terminate use of any peripheral devices if a connection to the A.C. main supply is detected 520, the application software and associated modules request confirmation from the system user that isolation hardware is being used 524. If the system user confirms that appropriate isolation hardware is installed and operating, any normal hardware and software functionality is enabled 508, and usage of the peripheral device is allowed; if isolation hardware is not in place or operating, then peripheral device usage is disallowed. Such a confirmation 524 can be manually confirmed by the system user, and/or through input/output devices configured to determine the presence of isolation hardware, such as isolation transformers and devices.

Figure 6:
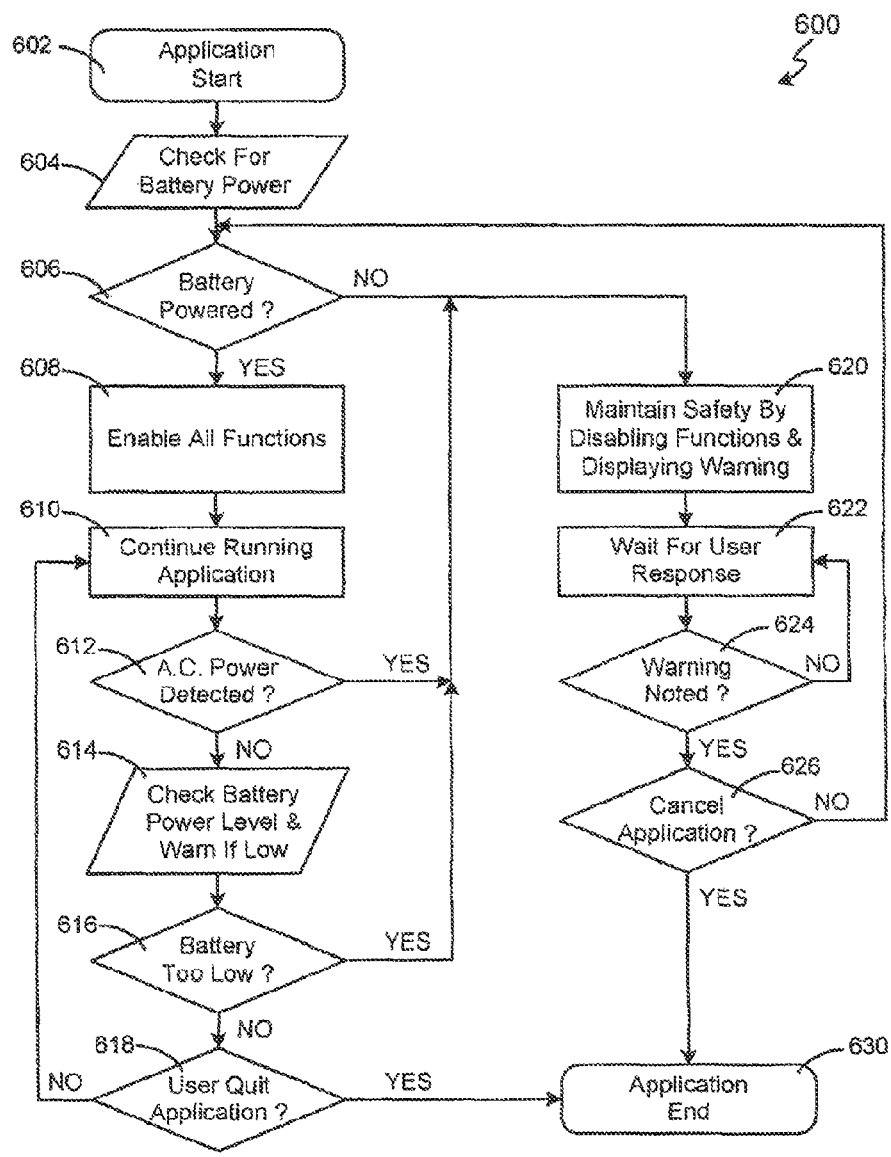
FIG. 6 is a flowchart of a A.C. detection software module in accordance with another exemplary embodiment of the present invention.

With reference to FIG. 6, another exemplary method may comprise additional monitoring and/or isolation functions. For example, as soon as the application software initiates or starts 602, the detection module checks for operative connection to an unisolated power supply, e.g., the A.C. supply, or to an isolated power supply, e.g., to battery power 604. If not battery powered (e.g., if powered by A.C. supply) the detection module moves to disabling functions and/or displaying a warning 620. However, if the detection module determines the host computer is powered directly by battery supply (e.g., the batter charger is not plugged in to the A.C. supply) 606, all normal hardware and software functionality is enabled 608, and the system continues operating or running 610 while the presence of A.C. charging is constantly scanned for by the detection module 612, e.g., the presence of A.C. charging is constantly scanned in the detection software and/or detected instantly via operating system interrupts, such as power change broadcast messages. Thereafter, if the connection to A.C. power is detected, the detection module moves to disabling functions and/or displaying a warning 620. However, if no such detection occurs, the detection module also checks whether the battery level has gone low. If the battery supply level is low, a warning can be issued to the user 614. If the battery level goes too low, e.g. almost empty, the detection module can also resort to disabling functions 620 to maintaining safety, and/or the user can request to quit the application 618 and end operation 630, or to continue the application running 610.

The process of disabling/warning 620 maintains safety by disabling functions (hardware and/or software), displaying a warning, and/or waiting for a user acknowledgement 622 if a connection to A.C. power is detected or the battery is very low or nearly empty. For example, as a warning is acknowledged 624, the user can be given the option to cancel the application 626 and thereby ending 630; if the user decides not to cancel operation, the detection module can continue with monitoring/re-checking for battery power 606. Thus, the system functionality in which safety and patient isolation is essential can be controlled such that the functionality is not re-enabled until the system is confirmed to be supplied on battery power. Such a configuration can allow the user to perform some functions, such as saving images or other processes, while safety-critical features and patient isolation can be preserved.

Figure 7A:
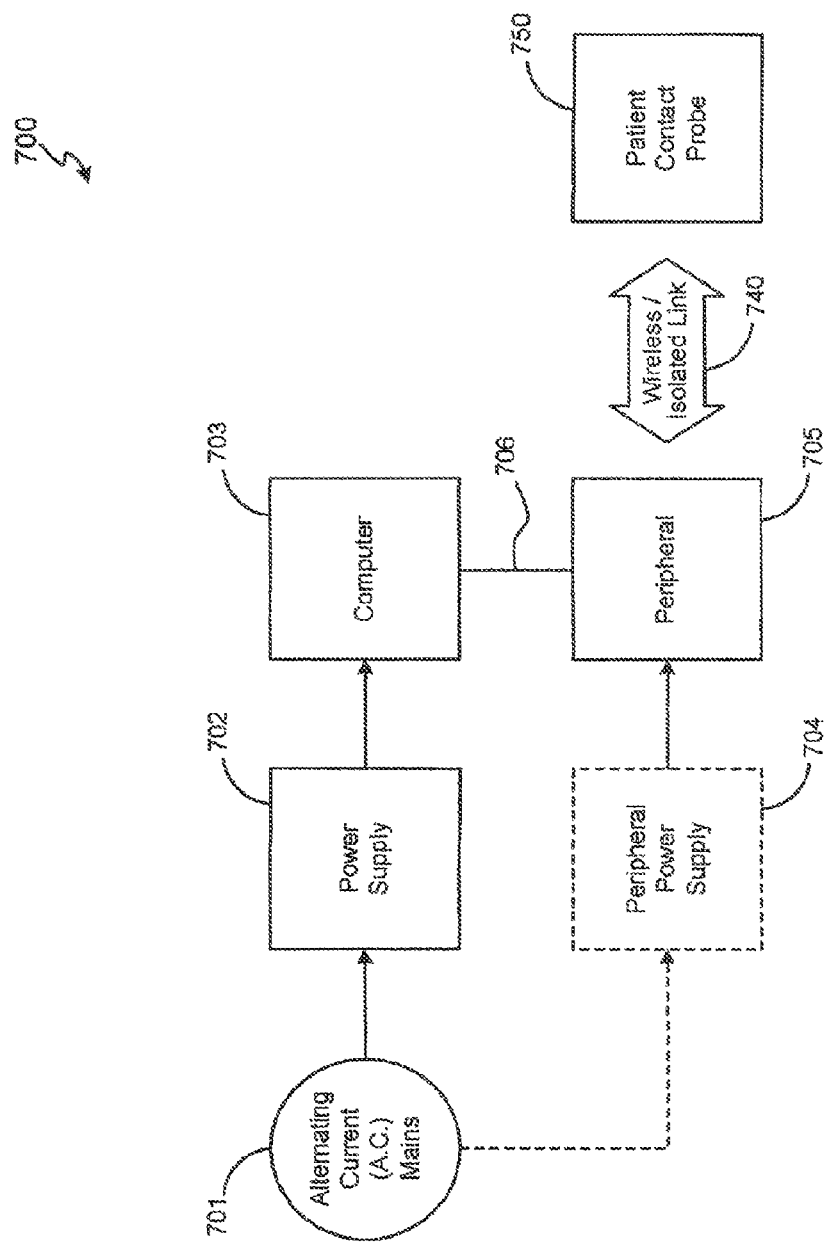
FIGS. 7A and 7B are block diagrams of exemplary systems for enhancing electrical safety of peripheral systems with an isolation subsystem comprising a wireless or other isolated link to a patient contact probe in accordance with an exemplary embodiment of the present invention.
Figure 7B:
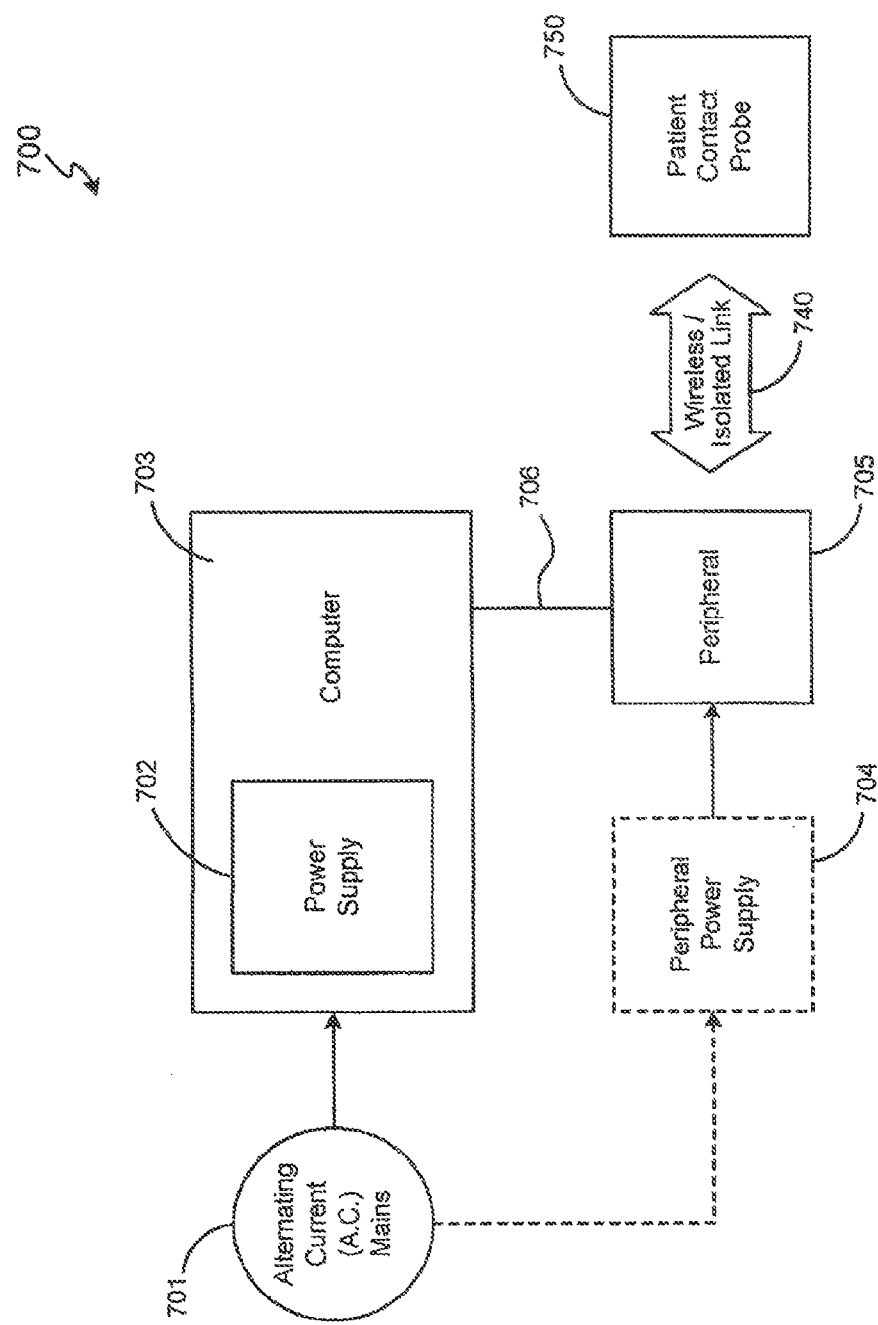

In accordance with another exemplary embodiment, with reference to FIG. 7A (laptop or portable PC) and 7B (desktop PC), peripheral safety system 700 can include an isolation subsystem comprising a wireless and/or other isolated electrical link 740 coupled between a peripheral system 705 and a peripheral device 750, such as a patient contact probe. Some examples of wireless and/or other isolated electrical links include wireless USB (wireless Universal Serial Bus), certified wireless USB, wireless Ethernet or IEEE 802.11 based technology, Wi-Fi, WiMedia, Bluetooth, proprietary radio transceivers and associated technology, cellular or other radio network based wireless, and optical wireless such as IrDA. By providing a wireless and/or electrically safe or low-leakage isolated link 740 between the peripheral/computer and patient contact probe 750, patient safety is enhanced. Isolated link 740 may be provided at any suitable point within system 700. For example, components, part or whole, of computer 703 and/or peripheral 705 may be disposed on either side of isolated link 740, so long as a high degree of isolation between A.C. main supply 701 and patient are maintained.

Figure 8A:
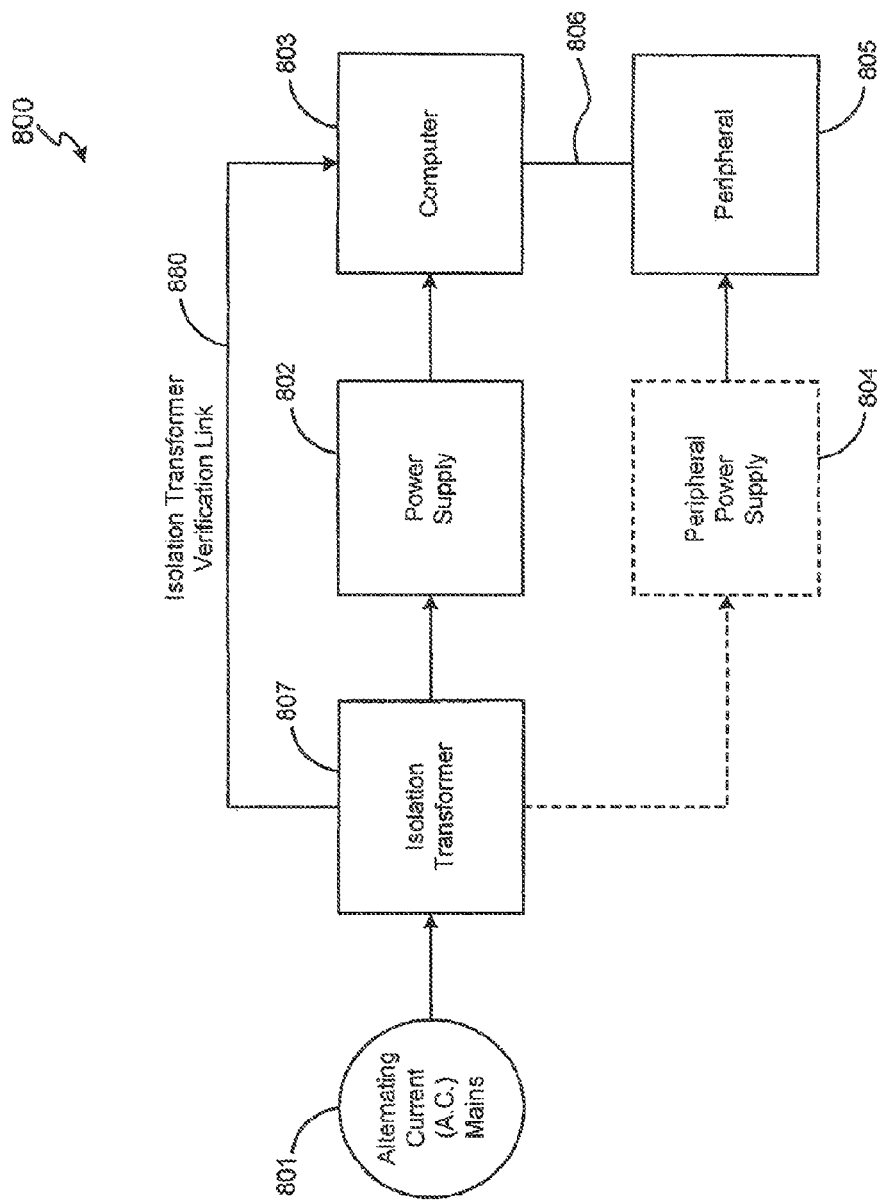
FIGS. 8A and 8B are block diagrams of exemplary systems for enhancing electrical safety of peripheral systems with an isolation subsystem comprising an isolation transformer verification link in accordance with an exemplary embodiment of the present invention.
Figure 8B:
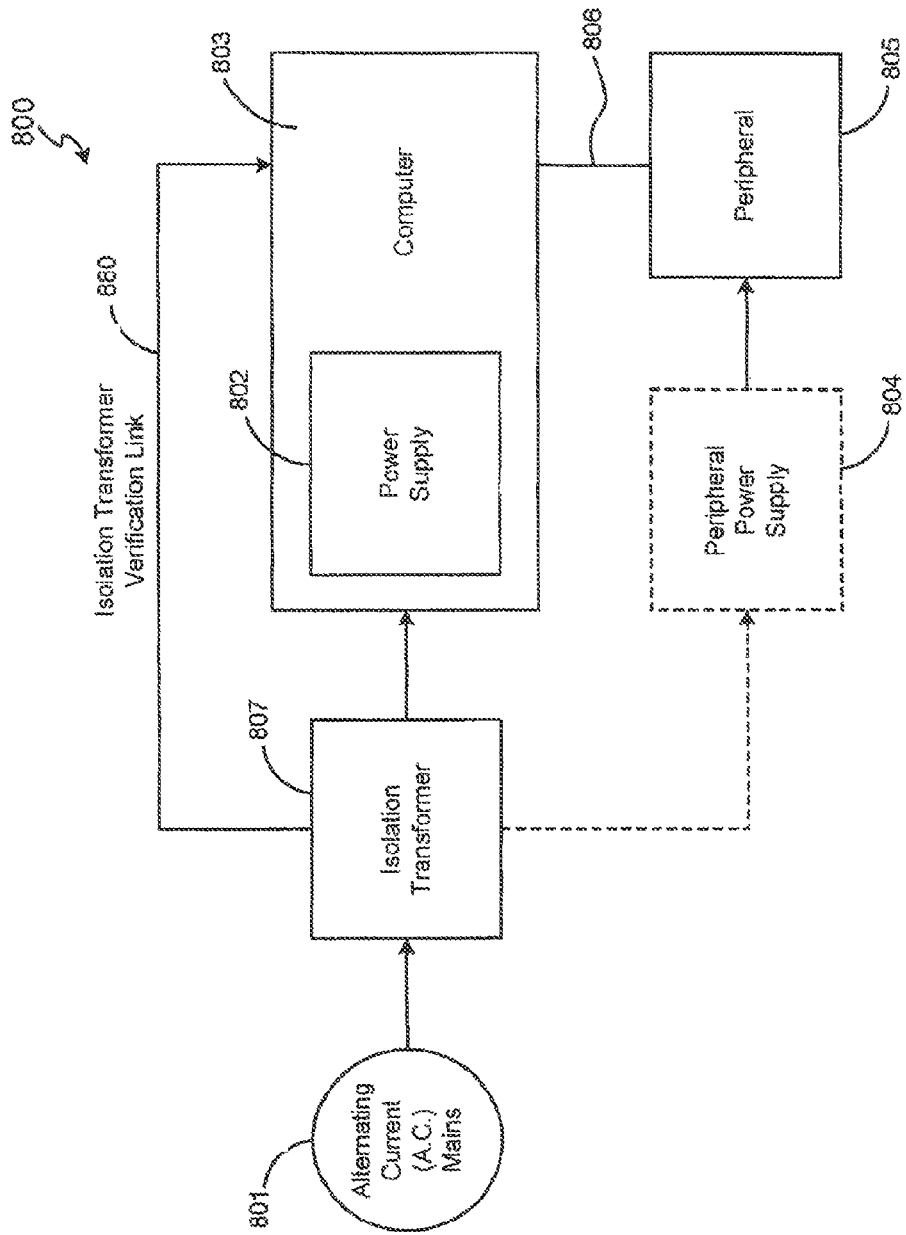

In accordance with another exemplary embodiment of the present invention, with reference to FIG. 8A (laptop or portable PC) and 8B (desktop PC), a peripheral safety system 800 can include an isolation subsystem comprising an isolation transformer 807 configured with an isolation transformer verification link 880 configured in between isolation transformer 807 and computer 803. Isolation transformer 807 can comprise a low-leakage medical-grade isolation transformer or other like systems. As such, isolation transformer 807 provides a high degree of electrical isolation only when it is used as intended, thus isolation transformer verification link 880 is configured to confirm with computer 803 and/or peripheral 805 that isolation transformer 807 is present and in proper use. Isolation transformer verification link 980 suitably comprises a feedback mechanism that can contain software and/or hardware functionality and protection keys to assure that isolation transformer 807 and/or other components in system 800 are being used in the appropriate configuration to maintain safety. Isolation transformer verification link 880 can comprise any feedback configuration configured to monitor an isolation transformer and/or other electrical or control components and/or any of the appropriate operations of peripheral device 805. For example, in accordance with an exemplary embodiment, isolation transformer verification link 880 can comprise a wire or other coupling device connected into a USB port of computer 803 from isolation transformer 807 to allow monitoring of transformer operation. However, isolation transformer verification link 880 can comprise any other communication link, e.g., cable and/or wireless.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. For example, although the exemplary embodiments illustrate one configuration for an isolation subsystem, it should be noted that various exemplary embodiments for an isolation subsystem can also comprise a combination of detection module and isolation transformer and/or wireless/isolated links. These and other changes or modifications are intended to be included within the scope of the present invention, as set forth in the following claims.

The invention claimed is:

1. A method of enhancing safety for a use of a peripheral device interfaced to a computer, the method comprising the steps of:
   providing an isolation subsystem coupled between an A.C. power supply and a peripheral medical device, wherein the isolation subsystem comprises a detection module configured within the computer;
   operating the peripheral medical device to deliver ultrasound;
   determining whether the host computer is powered by a battery or by the A.C. power supply during the operating the peripheral medical device;
   continuing the operating the peripheral medical device if the computer is powered by the battery;
   monitoring power levels of the battery during the operating the peripheral medical device; and
   warning a user if the power levels are below the acceptable levels.

2. The method according to claim 1, wherein the peripheral device comprises a therapeutic ultrasound peripheral.

3. The method according to claim 1, further comprising providing a signal from the computer to disable at least one function of peripheral medical device.

4. The method according to claim 3, wherein the signal is initiated by the computer based on the power levels.

5. The method according to claim 1, further comprising controlling the peripheral medical device with the computer.

6. The method according to claim 1, further comprising disabling at least one function of the peripheral medical device, if the computer is powered by the A.C. power supply.

7. The method according to claim 1, further comprising disabling at least one function of the peripheral medical device, if the computer is powered by the battery and if the power level of the battery is below a preset level.

8. The method according to claim 1, wherein the peripheral device comprises an ultrasound imaging peripheral.

9. A method for enhancing computer peripheral safety for use with medical applications, the method comprising the steps of:
   providing an isolation subsystem coupled between an A.C. power supply and a medical peripheral device coupled to a host computer by a wireless link between the medical peripheral device and the host computer, wherein the isolation subsystem comprises a detection module configured within the computer;
   monitoring power levels of a battery that powers the medical peripheral device via the wireless link during operation of the medical peripheral device to deliver ultrasound; and;
   disabling the medical peripheral device, if the power levels of the battery powering the medical peripheral device are below acceptable levels.

10. The method according to claim 9, wherein the medical peripheral device comprises a therapeutic ultrasound peripheral.

11. The method according to claim 9, wherein the medical peripheral device comprises an ultrasound imaging peripheral.

12. The method according to claim 9, further comprising disabling at least one function of the peripheral medical device, if the medical peripheral device is powered by the battery and if a power level of the battery is below a preset level.

13. The method according to claim 9, further comprising controlling the medical peripheral device with the host computer.

14. The method according to claim 9, further comprising providing a signal from the host computer to disable at least one function of the medical peripheral device.

15. The method according to claim 14, wherein the signal is initiated by the host computer based on feedback from the monitoring.

* * * * *